United States Patent

Prestel et al.

[11] Patent Number: 5,276,161
[45] Date of Patent: * Jan. 4, 1994

[54] PROCESS FOR THE PREPARATION OF BENZOTRIAZOLES

[75] Inventors: Helmut Prestel, Bruchsal; Rudolf Maul, Lorsch/Hessen, both of Fed. Rep. of Germany

[73] Assignee: Ciba-Geigy Corporation, Ardsley, N.Y.

[*] Notice: The portion of the term of this patent subsequent to Mar. 12, 2008 has been disclaimed.

[21] Appl. No.: 582,292

[22] Filed: Sep. 13, 1990

[30] Foreign Application Priority Data

Sep. 20, 1989 [CH] Switzerland ............ 3420/89

[51] Int. Cl.$^5$ .......................... C07D 249/18
[52] U.S. Cl. ..................... 548/260; 548/259
[58] Field of Search ............... 548/259, 260

[56] References Cited

U.S. PATENT DOCUMENTS

| | | | |
|---|---|---|---|
| 3,978,074 | 8/1976 | Jancis | 260/308 B |
| 4,219,480 | 8/1980 | White et al. | 548/260 |
| 4,230,867 | 10/1980 | Kintopf et al. | 548/260 |
| 4,999,433 | 3/1991 | Prestel et al. | 548/260 |
| 5,187,289 | 2/1993 | Fukuoka et al. | 548/260 |

FOREIGN PATENT DOCUMENTS

| | | |
|---|---|---|
| 380839 | 8/1990 | European Pat. Off. ........... 548/260 |
| 52-113973 | 9/1977 | Japan . |
| 52-113974 | 9/1977 | Japan . |
| 1494823 | 12/1977 | United Kingdom . |
| 1494824 | 12/1977 | United Kingdom . |
| 1494825 | 12/1977 | United Kingdom . |

*Primary Examiner*—Patricia L. Morris
*Attorney, Agent, or Firm*—Luther A. R. Hall

[57] ABSTRACT

2-(2-Hydroxyphenyl)-2H-benzotriazoles of the formula

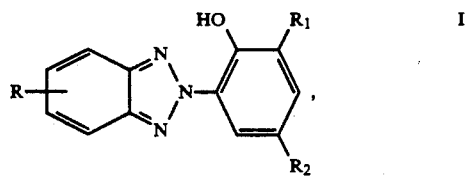

in which R is hydrogen, $C_1$–$C_{12}$alkyl or $C_1$–$C_4$alkoxy, $R_1$ is hydrogen, $C_1$–$C_{12}$alkyl, $C_5$–$C_6$cycloalkyl, phenyl or phenyl-$C_1$–$C_4$alkyl and $R_2$ is $C_1$–$C_{12}$alkyl, $C_5$–$C_6$cycloalkyl, phenyl, phenyl-$C_1$–$C_4$alkyl or a group —$C_nH_{2n}$—$COOR_3$, in which n is 0 to 4 and $R_3$ is hydrogen or $C_1$–$C_{12}$alkyl, can be prepared particularly advantageously by catalytic hydrogenation of a suitable o-nitroazo compound in the presence of a Pt, Pd, Pt/Pd or Rh hydrogenation catalyst and an alkylenediamine or an acyclic or cyclic polyalkylene polyamine in a halogenated or nonhalogenated aromatic hydrocarbon as solvent.

15 Claims, No Drawings

PROCESS FOR THE PREPARATION OF BENZOTRIAZOLES

The present invention relates to a process for the preparation of 2-(2-hydroxyphenyl)-2H-benzotriazoles by catalytic hydrogenation of o-nitrophenylazohydroxyphenyl compounds in the presence of a noble metal hydrogenation catalyst and of certain organic amines.

2-(2-Hydroxyphenyl)-2H-benzotriazoles are known from the literature as valuable UV absorbers. They are widely used in practice as light stabilizers for a large number of substrates, for example for stabilizing thermoplastics and coating materials (for example varnishes), but also in various recording materials (for example in photographic layers and papers and in printing inks and printing papers) and in textiles.

In accordance with the importance of these compounds, an extremely large number of processes for their preparation has already been proposed. The majority of them start from the abovementioned o-nitrophenylazo compounds and utilize reductive cyclization by various reduction methods. One of these reduction methods is catalytic hydrogenation, which has been described in a series of publications for the benzotriazoles mentioned.

U.S. Pat. No. 3,978,074 describes a hydrogenation process of the abovementioned type which is carried out in alkaline and preferably in aqueous medium and in which the conventional noble metal and other metal catalysts are used as hydrogenation catalysts. According to GB-A 1,494,825 and 1,494,824, the hydrogenation is likewise carried out in a purely aqueous alkaline (GB-A 1,494,825) or aqueous/organic (GB-A 1,494,824) medium. The hydrogenation catalysts used are noble metals. The hydrogenation process described in GB-A 1,494,823 is carried out in organic solvents with the use of organic amines as bases and the conventional noble metal catalysts. U.S. Pat. No. 4,219,480 teaches the use of a nickel catalyst as hydrogenation catalyst.

JP-A 52/113,973 and 52/113,974 also relate to the preparation of 2-(2-hydroxyphenyl)-2H-benzotriazoles by catalytic hydrogenation. The catalysts used also include 5% platinum on carbon. In the second-mentioned Japanese publication, polyalkyl polyamines are also described as bases, but in all exemplary embodiments the use of a water-miscible solvent (an alcohol) is intended. The yields obtained are relatively low.

Surprisingly, it has now been found that the reduction process mentioned can be carried out particularly advantageously and economically by using a certain class of amines and certain solvents.

The process according to the invention for the preparation of 2-(2-hydroxyphenyl)-2H-benzotriazoles of the formula

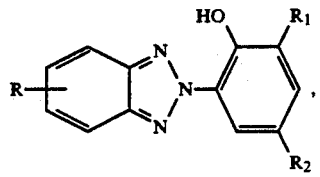

in which R is hydrogen, $C_1$-$C_{12}$alkyl or $C_1$-$C_4$alkoxy, $R_1$ is hydrogen, $C_1$-$C_{12}$alkyl, $C_5$-$C_6$cycloalkyl, phenyl or phenyl-$C_1$-$C_4$alkyl and $R_2$ is $C_1$-$C_{12}$alkyl, $C_5$-$C_6$cycloalkyl, phenyl, phenyl-$C_1$-$C_4$alkyl or a group —$C_nH_{2n}$—$COOR_3$, in which n is 0 to 4 and $R_3$ is hydrogen or $C_1$-$C_{12}$alkyl, by catalytic hydrogenation of an azo compound of the formula

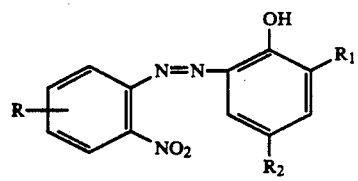

in the presence of a noble metal hydrogenation catalyst and an organic amine comprises using Pt, Pd, Pt/Pd or Rh on a support as hydrogenation catalyst and an alkylenediamine or an acyclic or cyclic polyalkylene polyamine as amine, in which the nitrogen atoms of the amines mentioned are unsubstituted or, independently of one another, substituted by $C_1$-$C_6$alkyl, and carrying out the hydrogenation in an aromatic hydrocarbon or halogenated aromatic hydrocarbon or mixtures of the hydrocarbons mentioned with water as solvent, which hydrogenation of azo compounds of the formula II, in which $R_2$ is —$C_nH_{2n}$COOH, is carried out in water or in mixtures of the hydrocarbons mentioned and water.

In formula I, phenyl-$C_1$-$C_4$alkyl ($R_1$, $R_2$) is preferably benzyl, phenethyl, α-methylbenzyl and α,α-dimethylbenzyl, in particular benzyl or α,α-dimethylbenzyl. $R_3$ is preferably H or $C_1$-$C_4$alkyl, in particular H or methyl. From the lower alkyl esters, in particular the methyl ester, it is possible, for example by subsequent hydrolysis, to prepare compounds where $R_3$ is H or, by transesterification, compounds containing other alkyl groups $R_3$. In particular cyclohexyl is suitable as cycloalkyl. Alkyl groups R, $R_1$, $R_2$ or $R_3$ have preferably 1 to 8, in particular 1-5 C atoms.

The starting compounds of the formula II are known, for example from the publications mentioned at the beginning or from EP-A 57,160, or they can be prepared by the methods mentioned, there for example by diazotization of an o-nitroaniline of the formula

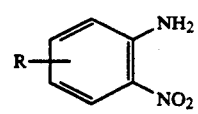

and coupling of the resulting diazonium salt onto a phenol of the formula

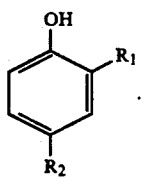

Compounds of the formula I in which R is hydrogen or $C_1$-$C_{12}$alkyl, in particular hydrogen, for example those compounds of the formula I in which $R_1$ is hydrogen, $C_1$-$C_{12}$alkyl or phenyl-$C_1$-$C_3$alkyl (in particular α,α-dimethylbenzyl) and $R_2$ is $C_1$-$C_{12}$alkyl (for example $C_1$-$C_8$alkyl), phenyl-$C_1$-$C_3$alkyl (in particular α,α-dimethylbenzyl) or a group —$C_2H_4COOR_3$, in which $R_3$ is H or $C_1$–$C_{12}$alkyl (for example $C_1$–$C_8$alkyl), in particular H or $C_1$–$C_4$alkyl, are preferably prepared.

Of particular practical importance is the preparation of compounds of the formula I in which $R_1$ is hydrogen or $C_1$–$C_8$alkyl and $R_2$ is $C_1$–$C_8$alkyl.

The hydrogenation catalysts used according to the invention are Pt, Pd, Pt/Pd or Rh on a support. Suitable supports are those customary in the technology of hydrogenation catalysts, for example carbon (for example activated carbon, charcoal, peat charcoal), kieselguhr, alumina, barium sulfate and the like. Carbon is preferred as support. Preferred catalysts according to the invention are Pt, Pd or Pt/Pd, in particular Pt, on carbon catalysts.

The amount of noble metal on the support (amount deposited) is in the range customary for hydrogenation catalysts. It is, for example, 0.1 to 10%, for example 0.5 to 10%, preferably 1 to 10%, in particular 3 to 10%. Amounts of 3 to 7%, for example about 5%, in each case relative to the weight of the support material, are particularly advantageous.

The catalyst is advantageously used in an amount of 0.1–6%, in particular 0.5–4%, for example 1.0–3%, relative to the o-nitroazo compound used. It will be appreciated that the catalyst is recyclable, advantageously by filtration, if the process is carried out batchwise.

Suitable alkylenediamines are in particular those having 1 to 8, preferably 1 to 6, especially 2 to 8, for example 2 to 6, C atoms, it being possible for the alkylene group to be straight-chain or branched. The amino groups of the alkylenediamines can be substituted by $C_1$–$C_6$-, preferably $C_1$–$C_4$alkyl groups. Thus the alkylenediamines can be substituted by a maximum of 4 alkyl groups, although preferably at least one NH or $NH_2$ group is present in the molecule. Preferred alkyl substituents are methyl groups or ethyl groups. Examples are ethylenediamine, n-propylenediamine, n-butylenediamine, n-pentylenediamine, n-hexylenediamine, 1-amino-2-methylaminoethane, 1-amino-3-methylaminopropane, 1-amino-4-methylaminobutane, 1-amino-3-dimethylaminopropane, 1-amino-3-diethylaminopropane etc. Acyclic polyalkylene polyamines are, for example, those having 3 to 6 amine functions and 2 to 28, for example 2 to 20, preferably 4 to 18, in particular 4–12, C atoms. Suitable polyalkylene polyamines have the formula $(R_0)_2N$–$C_nH_{2n}(NR_o$–$C_nH_{2m})_p$–$N(R_o)_2$, in which p is a number from 0 to 4 and m and n, independently of one another, are a number from 1 to 6, in particular 1 to 4, it being possible for the individual indices m, in the case where p>1, to be identical or different, and the $R_o$ to be identical or different and being hydrogen or $C_1$–$C_6$-, in particular $C_1$–$C_4$alkyl, especially methyl or ethyl. $R_o$ is preferably hydrogen. The alkylene chains are preferably unbranched radicals. The sum of all n+m is preferably 2–20, in particular 4–18, for example 4–12. The index p is preferably a number from 1 to 3, in particular 1 or 2. In the case where amino groups are substituted by alkyl groups, all amino groups can be substituted by the alkyl groups mentioned. However, preferably, at least one —NH— or —$NH_2$— group is present in the molecule. A polyalkylene polyamine preferably contains 1 to 3, for example 1 or 2, in particular one alkyl substituent.

Particularly suitable polyalkylene polyamines have the formula $(R_o)_2N$—$(CH_2)_{n'}$—$NR_o$—$(CH_2)_{m'}$, —$[N$-$R_o$—$(CH_2)_{p'}]_q$—$N(R_o)_2$, in which n', m' and p', independently of one another, are 2 to 4 and q is 0, 1 or 2, in particular 0 or 1.

Examples of polyalkylene polyamines are diethylenetriamine, triethylenetetramine, di-n-or iso-propylenetriamine, tri-n- or -iso-propylenetetramine, di-n-butylenetriamine and tri-n-butylenetetramine, $H_2N(CH_2)_3N(CH_3)(CH_2)_3NH_2$, $H_2N(CH_2)_2N(CH_3)(CH_2)_2NH_2$, $H_2N(CH_2)_2N(CH_3)(CH_2)_2NH(CH_3)(CH_2)_2NH_2$, $CH_3NH(CH_2)_2NH(CH_2)_2NHCH_3$ etc.

Examples of cyclic polyalkylene polyamines are saturated mono- or polynuclear heterocyclic rings containing at least 2 nitrogen atoms. The individual heterocycles are in particular 5-to 7-membered, for example 6-membered. Examples of mononuclear cyclopolyalkylene polyamines are imidazolidine, pyrazolidine, hexahydropyrimidine, hexahydropyrazine and piperazine. Examples of the polynuclear cyclopolyalkylene polyamines are triethylenediamine (diazabicyclooctane), diazabicyclononane, diazabicycloundecane and hexamethylenetetramine. In as far as the cyclic amines mentioned contain NH groups, these can be likewise substituted by $C_1$–$C_6$-, in particular $C_1$–$C_4$alkyl groups, preferably methyl groups. Examples are N-methylpiperazine and N,N-dimethylpiperazine.

The amines used in the process according to the invention are advantageously $C_1$–$C_8$alkylenediamines substituted on one or more nitrogen atoms by methyl groups or ethyl groups or polyalkylene polyamines having 3 to 6 amine functions and 2 to 28, in particular 2 to 20, C atoms, piperazine, N-methylpiperazine, triethylenediamine or hexamethylenetetramine. Preferred amines are $C_2$–$C_6$alkylenediamines or polyalkylene polyamines of the formula $H_2N$—$(CH_2)_{n'}NH$—$(CH_2)_{m'}$—$[NH$—$(CH_2)_{p'}]_q$—$NH_2$, in which the general symbols are as defined above and one or more nitrogen atoms can be substituted by methyl groups or ethyl groups, or piperazine, N-methylpiperazine or triethylenediamine. Particularly preferred amines are ethylenediamine, n-propylenediamine, 1-amino-3-dimethylamino-n-propane, 1-amino-3-diethylamino-n-propane, n-butylenediamine, n-pentylenediamine, n-hexylenediamine, diethylenetriamine, triethylenetetramine, di-n-propylenetriamine, tri-n-propylenetetramine, di-n-butylenetriamine or tri-n-butylenetetramine, 1-amino-2-methylaminoethane, 1-amino-3-methylaminopropane, $H_2N(CH_2)_3N(CH_3)(CH_2)_3NH_2$, piperazine, N-methylpiperazine or triethylenediamine, in particular ethylenediamine, n-propylenediamine, diethylenetriamine, triethylenetetramine or piperazine, in particular ethylenediamine.

It is of course also possible to use mixtures of two or more of the amines mentioned in the process according to the invention.

The organic amine is present in the reaction mixture advantageously in an amount of at least 0.01 mole, in particular at least 0.1 mole, preferably at least 0.4 mole, up to about 8 mole per mole of o-nitroazobenzene starting material. Molar ratios of amine:azo compound are particularly advantageously in the range of about 0.5:1 to 1:1, in particular about 1:1.

In the process according to the invention (if $R_3$ is not equal to H), an aromatic hydrocarbon (for example benzene or alkyl-substituted benzenes) or halogenated aromatic hydrocarbons (for example chlorinated benzenes such as chlorobenzene, dichlorobenzene and trichlorobenzene) function as solvents. Aromatic hydrocarbons are preferred, in particular benzene, toluene or xylenes. Mixtures of the solvents mentioned can also be used. If halogenated hydrocarbons are used as solvents, the reaction is preferably carried out under mild hydrogenation conditions. Nor does the presence of water interfere in the process according to the invention, for example in amounts of up to 50%, for example up to 30%, relative to the total amount of solvent. However, the process according to the invention is carried out in the absence of water-miscible organic solvents (for example alcohols).

If an azo compound of the formula II in which $R_2$ is $C_nH_{2n}$—COOH is used as starting material, the hydrogenation is carried out in water or a mixture of water and a halogenated or non-halogenated aromatic hydrocarbon as solvent. Preferred hydrocarbons are the ones mentioned above. In this case, the solvent system advantageously contains the amount of water necessary for dissolving the final product (in order to enable the catalyst to be separated off, for example by filtration), preferably at least 30%, in particular at least 50%, especially at least 70% of water.

The process according to the invention can be carried out batchwise but also continuously. For the continuous process, in particular a fixed bed catalyst, for example a high-pressure fixed bed hydrogenation unit, is suitable. In this case the reaction mixture is removed continuously and fed with fresh nitroazo compound+amine+-solvent.

A particularly advantageous variation of the process according to the invention, which allows a continuous process and leads to high conversions and short reaction times, consists in initially introducing the catalyst in a portion of the solvent into an autoclave, putting the autoclave under a hydrogen pressure, and then metering in the corresponding compound of the formula II, dissolved or dispersed in a further portion of the solvent, for example by means of a metering pump. The reaction solution can then be removed continuously, and the final product can be isolated therefrom in a conventional manner. Alternatively, it is also possible to filter off the catalyst in a batchwise process, and work up the filtrate correspondingly.

The hydrogenation is advantageously carried out at temperatures of 0°–120° C., for example 15°–100° C., in particular 20°–80° C. Reaction temperatures of 25°–70° C., in particular 40°–70° C., for examples 50°–60° C., are particularly advantageous.

The hydrogen pressure during the hydrogenation can be, for example, in the range from 1–200, for example 1–100, in particular 5–50, preferably 10–20. Which hydrogen pressure is employed depends mainly on the hydrogenation unit available. In high pressure units, pressures of 100–200 bar are possible. These are in particular customary in a continuous process.

The hydrogenation time can vary within wide limits; it depends on the catalyst used, the hydrogen pressure, the reaction temperature and the unit used. It can be, for example, from 30 seconds to 5 hours, in particular 10 minutes to 3 hours, for example 10 minutes to 2 hours. In a continuous process, residence times of, for example, 1 to 60 minutes, in particular 1 to 30 minutes, can be expected in practice.

The isolation of the final products from the reaction medium is carried out by conventional methods known to one skilled in the art. It varies, depending on the type of solvent used. An advantageous method consists in precipitating the reaction mixture, which may have been concentrated before, by adding a solvent in which the particular final product is sparingly soluble and by filtering off the precipitate. Work up and purification operations, if carried out, can be seen from the examples.

As already mentioned at the beginning, the 2-(2-hydroxyphenyl)-2H-benzotriazoles preparable according to the invention represent valuable UV absorbers which can be used in practice as light stabilizers for a large number of applications (such as the ones listed in the introduction). Detailed possible applications of the benzotriazoles mentioned are described in U.S. Pat. Nos. 3,055,896, 3,004,896, 3,072,585, 3,074,910, 3,189,615 and 3,230,194. The process according to the invention opens up an industrially particularly favourable and economical route for their preparation.

The examples which follow illustrate the process according to the invention in more detail. Therein and also in the remaining description and patent claims, parts and percentages are by weight, unless stated otherwise.

EXAMPLE 1

2-(2'-hydroxy-5'-methylphenyl)-2H-benzotriazole 60 g of 2-nitro-2'-hydroxy-5'-methylazobenzene (91% pure), 1.2 g of 5% Pt on activated carbon, 80 g of xylene and 20 g of diethylenetriamine are placed in a 300 ml hydrogenation reactor at room temperature under argon. Argon is then replaced by hydrogen. After injecting 10 bar of hydrogen, the hydrogenation is carried out at 60° C. with vigorous stirring. The heat which is released is removed by cooling. The end of the hydrogenation reaction can be easily detected by the stoppage of the hydrogen absorption after 2 mole equivalents of hydrogen, relative to the azobenzene starting material. The total hydrogenation time is about 0.7 hour.

After heating the reaction mass to 80° C., the catalyst is filtered off. The reaction solution consists of a black, amine-rich bottom phase and a yellow to slightly brownish xylene top phase containing the product. The amine-rich bottom phase is separated off for the purpose of better work up and reuse of the amine.

By adding 20 g of water (at 70°–75° C.) to the phase containing the product and then separating off the aqueous amine phase, the diethylenetriamine is extracted from the xylene phase virtually quantitatively. The remaining xylene product phase is then concentrated by distillation in vacuo. The product is precipitated by adding 160 g of methanol (starting at about 90° C. with subsequent cooling under reflux). After cooling the crystalline dispersion to 0° C., the crystals are filtered off and dried. Yield: 44.0 g of the title compound, which corresponds to 92% of theory. Melting point 128° C.

EXAMPLES 2–4

Example 1 is repeated, except that 30 g of toluene and 70 g of diethylenetriamine are used instead of 80 g of xylene and 20 g of diethylenetriamine. No effect on the yield can be observed. Nor does the substitution of diethylenetriamine by triethylenetetramine or by ethylenediamine have any adverse effect. In each case, virtually the same yield as mentioned in Example 1 is obtained.

EXAMPLES 5–8

Examples 1 to 4 are repeated, except that the hydrogenation pressure is increased from 10 to 80 bar of hydrogen. This reduces the hydrogenation time from 0.7 hour to 0.3 hour. The work up is analogous, to give in each case virtually the same yield.

EXAMPLES 9–13

Example 1 is repeated, except that the same amount of a 1%, 2%, 3%, 4% and 10% Pt on activated carbon catalyst is used instead of a 5% Pt on activated carbon catalyst. The hydrogenation time continuously decreases with increasing amount of Pt deposited on the catalyst. It is about 3 hours for the 1% Pt catalyst and about 0.5 hour for the 10% Pt catalyst. The work up is analogous. The product yield obtained is hardly affected by the different amount of noble metal deposited on the catalyst. The product is isolated in a yield of 90±2% of theory.

EXAMPLES 14 and 15

Example 1 is repeated, except that the hydrogenation temperature is reduced from 60° C. to 30° C. or increased from 60° C. to 80° C. Apart from the effect on the hydrogenation time (prolonging to about 5 hours in the first case and shortening to about 0.5 hour in the second case), no significant effect is observed. The product is isolated in a similar yield to that in Example 1.

EXAMPLE 16

100 g of diethylenetriamine, 100 g of xylene and 6 g of 5% Pt on activated carbon are placed in a 2 l hydrogenation reactor at room temperature under argon. The reactor is sealed and argon is replaced by hydrogen. After injecting 10 bar of hydrogen, the catalyst is dispersed by vigorous stirring. At the same time, 300 g of 2-nitro-2'-hydroxy-5'-methylazobenzene (91% pure) are dispersed in 300 g of xylene and 40 g of water at room temperature in an external container. This dispersion is pumped into the hydrogenation reactor against the hydrogen pressure by means of an automatic metering unit over a period of one hour. This leads to the hydrogenation of the azo compound at 60° C. to give the corresponding benzotriazole.

After the metering is completed, the reaction mass is heated to 80° C., and the catalyst is filtered off. The further work up is carried out analogously to Example 1, using accordingly increased amounts of solvent. This gives 221 g of 2-(2'-hydroxy-5'-methylphenyl)-2H-benzotriazole, which corresponds to 92.5% of theory. Melting point: 128° C.

EXAMPLES 17–19

Example 1 is repeated, except that the same amount of a Pd/Pt mixed catalyst (4% Pd/1% Pt on activated carbon) or of a 5% Pd on activated carbon catalyst is used instead of the 5% Pt on activated carbon catalyst. Virtually no effect on the hydrogenation time can be observed. The product is isolated analogously to Example 1 in a yield of 90% of theory.

If a 5% Rh on activated carbon catalyst is used and the same procedure is followed, the product is isolated in a yield of 88% of theory.

EXAMPLE 20

Example 1 is repeated, except that in addition 8 g of water are added to the hydrogenation solution. No effect on the yield or hydrogenation time can be observed. The product is isolated in a yield of 92% of theory.

EXAMPLE 21

2-(2'-hydroxy-5'-tert.-octylphenyl)-2H-benzotriazole

Example 1 is repeated, except that an equivalent amount of 2-nitro-2'-hydroxy-5'-tert.-octylazobenzene (93% pure) is used instead of 2-nitro-2'-hydroxy-5'-methylazobenzene and a mixture of 60 g of xylene and 40 g of diethylenetriamine instead of 80 g of xylene and 20 g of diethylenetriamine. The hydrogenation is carried out at 45° C. The title product is isolated in a yield of 92% of theory. Melting point: 101°–103° C.

EXAMPLE 22

2-(2'-hydroxy-3',5'-di-tert.-butylphenyl)-2H-benzotriazole

Example 1 is repeated, except that an equivalent amount of 2-nitro-2'-hydroxy-3', 5'-di-tert.-butylazobenzene (91% pure) is used instead of 2-nitro-2'-hydroxy-5'-methylazobenzene and a mixture of 40 g of xylene and 60 g of diethylenetriamine instead of 80 g of xylene and 20 g of diethylenetriamine. The hydrogenation is carried out at 50° C. After work up of the hydrogenation solution, the product is crystallized from a mixture of 40 g of xylene and 160 g of methanol. The product (title compound) is isolated in a yield of 90% of theory. Melting point: 152°–154° C.

EXAMPLE 23

2-(2'-hydroxy-3'-isobutyl-5'-tert.-butylphenyl)-2H-benzotriazole

Example 22 is repeated, except that the same amount of 2-nitro-2'-hydroxy-3'-isobutyl-5'-tert.-butylazobenzene (86% pure) is used instead of the azo compound used there.

The hydrogenation is carried out at 40°–50° C.; the hydrogenation time is about 0.7 hour. After the catalyst has been filtered off and the amine bottom phase has been separated off, the remaining reaction solution is extracted twice (at 70°–75° C.) with 20 g of water each time. This removes the amine virtually quantitatively from the reaction solution.

After distilling off the xylene, 160 g of methanol are added to the remaining product melt at 60°–70° C. The product (title compound) crystallizes by slow cooling and seeding at 50°–60° C. After cooling to 0° C. and filtration and drying, the title compound is obtained in a yield of 87% of theory. Melting point: 79°–80° C.

EXAMPLE 24

2-(2'-hydroxy-3', 5'-di-tert.-amylphenyl)-2H-benzotriazole

Example 1 is repeated, except that an equivalent amount of 2-nitro-2'-hydroxy-3', 5'-di-tert.-amylazobenzene (91.6% pure) is used instead of 2-nitro-2'-hydroxy-5'-methylazobenzene and a mixture of 60 g of xylene and 40 g of diethylenetriamine is used instead of 80 g of xylene and 20 g of diethylenetriamine. The work up is analogous (filtering off the catalyst, separating off the amine bottom phase, extracting the remaining amine from the xylene top phase with water, concentration and crystallization from xylene/methanol). The title product is isolated in a yield of 86.5% of theory. Melting point: 80°–82° C.

EXAMPLE 25

2-(2'-hydroxy-3', 5'-bis-α,α-dimethylbenzylphenyl)-2H-benzotriazole

Example 22 is repeated, except that an equivalent amount of 2-nitro-2'-hydroxy-3', 5'-bis-α,α-dimethylbenzylazobenzene (90.3% pure) is used instead of the azo compound used there.

The hydrogenation temperature is 40° C. instead of 50° C. After work up of the hydrogenation solution, the product is crystallized from xylene/methanol (ratio: product/xylene/methanol=1:1:3). The title product is isolated in a yield of 92.5% of theory. Melting point: 137°-138° C.

EXAMPLE 26

2-[2'-hydroxy-3'-tert.-butyl-5'-(2''-methoxycarbonylethyl)phenyl]-2H-benzotriazole Example 1 is repeated, except that an equivalent amount of 2-nitro-2'-hydroxy-3'-tert.-butyl-5'-(2''-methoxycarbonylethyl)azobenzene (99.4% pure) is used instead of the azo compound used there and the same amount of a 1% Pt on activated carbon catalyst is used instead of the 5% Pt on activated carbon catalyst. The hydrogenation is carried out at 40° C., and the hydrogenation time is about 1.2 hours.

After separating off the catalyst and the amine, the xylene product phase is concentrated, and the product (title compound) is precipitated by adding methanol (ratio of product: xylene:methanol about 1:1.5:4). The crystals are separated off and dried. The title compound thus obtained has a melting point of 125°-126° C.

EXAMPLES 27 and 28

2-(2'-hydroxy-5'-methylphenyl)-2H-benzotriazole

Example 1 is repeated, except that a mixture of 40 g piperazine hexahydrate and 60 g of xylene or of 18 g of piperazine and 60 g of xylene is used instead of 20 g of diethylenetriamine and 80 g of xylene.

The product is isolated analogously to Example 1 in both cases in a yield of 91% of theory (melting point 127°-128° C.).

EXAMPLES 29 and 30

Example 1 is repeated, except that 22 g of 1-amino-3-dimethylamino-n-propane or 27 g of 1-amino-3-diethylamino-n-propane are used instead of the diethylenetriamine. In the first case, the title product is obtained in a yield of 88% and in the second case in a yield of 86% of theory. Melting point: 128° C.

What is claimed is:

1. A process for the preparation of a 2-(2-hydroxyphenyl)-2H-benzotriazole of the formula

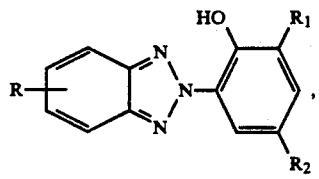

in which R is hydrogen, $C_1$–$C_{12}$alkyl or $C_1$–$C_4$alkoxy, $R_1$ is hydrogen, $C_1$–$C_{12}$alkyl, $C_5$–$C_6$cycloalkyl, phenyl or phenyl-$C_1$–$C_4$alkyl and $R_2$ is $C_1$–$C_{12}$alkyl, $C_5$–$C_6$cycloalkyl, phenyl, phenyl-$C_1$–$C_4$alkyl or a group —$C_nH_{2n}$—$COOR_3$, in which n is 0 to 4 and $R_3$ is hydrogen or $C_1$–$C_{12}$alkyl, by catalytic hydrogenation of an azo compound of the formula

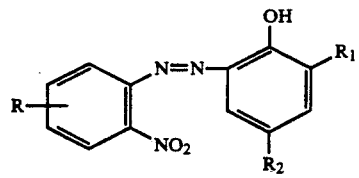

in the presence of a noble metal hydrogenation catalyst and an organic amine, which comprises using Pt, Pd, Pt/Pd or Rh on a support as hydrogenation catalyst and an alkylenediamine or an acyclic or cyclic polyalkylene polyamine as amine, in which the nitrogen atoms of the amines mentioned are unsubstituted or, independently of one another, substituted by $C_1$–$C_6$alkyl, and carrying out the hydrogenation in an aromatic hydrocarbon or halogenated aromatic hydrocarbon or mixtures of the hydrocarbons mentioned with water as solvent, the amount of water being less than 0.2 times the weight of the compound of formula II, which hydrogenation of azo compounds of the formula II, in which $R_2$ is —$C_nH_{2n}$COOH, is carried out in water or in mixtures of the hydrocarbons mentioned and water.

2. A process according to claim 1, wherein R is hydrogen or $C_1$–$C_{12}$alkyl.

3. A process according to claim 1, wherein $R_1$ is hydrogen, $C_1$–$C_{12}$alkyl or phenyl-$C_1$–$C_3$alkyl and $R_2$ is $C_1$–$C_{12}$alkyl, phenyl-$C_1$–$C_3$alkyl or a group —$C_2H_4$COOR_3$, in which $R_3$ is H or $C_1$–$C_{12}$alkyl.

4. A process according to claim 3, wherein $R_1$ is hydrogen or $C_1$–$C_8$alkyl and $R_2$ is $C_1$–$C_8$alkyl.

5. A process according to claim 1, wherein 0.1 to 10% Rh, Pt, Pd or Pt/Pd on carbon is used as catalyst.

6. A process according to claim 5, wherein 1-10% Rh, Pt, Pd or Pt/Pd on carbon is used as catalyst.

7. A process according to claim 1, wherein the organic amine used is a $C_1$–$C_8$alkylenediamine which is unsubstituted or substituted on one or more nitrogen atoms by methyl groups or ethyl groups, or is a polyalkylene polyamine having 3 to 6 amine functions and 2 to 28 C. atoms, or is piperazine, N-methylpiperazine, triethylenediamine or hexamethylenetetramine.

8. A process according to claim 7, wherein the organic amine is a $C_2$–$C_8$alkylenediamine or a polyalkylene polyamine of the formula $H_2N$—$(CH_2)_{n'}$—NH—$(CH_2)_{m'}$—[NH—$(CH_2)_{p'}]_q$—$NH_2$, in which n', m' and p', independently of one another, are 2 to 4, and q is 0, 1 or 2 and which is unsubstituted or substituted on one or more nitrogen atoms by methyl groups or ethyl groups, or is piperazine, N-methylpiperazine or triethylenediamine.

9. A process according to claim 7, wherein the amine is ethylenediamine, n-propylenediamine, 1-amino-3-dimethylamino-n-propane, 1-amino-3-diethylamino-n-propane, n-butylenediamine, n-pentylenediamine, n-hexylenediamine, diethylenetriamine, triethylenetetramine, di-n-propylenetriamine, tri-n-propylenetetramine, di-n-butylenetriamine, tri-n-butylenetetramine, 1-amino-2-methylaminoethane, 1-amino-3-methylaminopropane, $H_2N(CH_2)_3N(CH_3)(CH_2)_3NH_2$, piperazine, N-methylpiperazine or triethylenediamine.

10. A process according to claim 9, wherein the amine is ethylenediamine, n-propylenediamine, diethylenetetramine, triethylenetetramine or piperazine.

11. A process according to claim 1, wherein the solvent used is an aromatic hydrocarbon.

12. A process according to claim 11, wherein the solvent is benzene, toluene or a xylene.

13. A process according to claim 1, wherein, in the case that $R_2$ is $C_nH_{2n}$—COOH, water is used as solvent.

14. A process according to claim 1, wherein the amine is used in an amount of at least 0.01 mole per mole of azo compound of the formula II.

15. A process according to claim 14, wherein the molar ratio of amine to azo compound is about 0.5:1 to 1:1.

* * * * *